US012279764B2

United States Patent
Li et al.

(10) Patent No.: US 12,279,764 B2
(45) Date of Patent: Apr. 22, 2025

(54) FORWARD-PUSHING FOR RELEASING SUTURE LOCKING DEVICE

(71) Applicant: HANGZHOU VALGEN MEDTECH CO., LTD., Zhejiang (CN)

(72) Inventors: Yang Li, Zhejiang (CN); Weilin Liang, Zhejiang (CN); Tingchao Zhang, Zhejiang (CN)

(73) Assignee: HANGZHOU VALGEN MEDTECH CO., LTD., Hangzhou (CN)

( * ) Notice: Subject to any disclaimer, the term of this patent is extended or adjusted under 35 U.S.C. 154(b) by 368 days.

(21) Appl. No.: 17/948,402

(22) Filed: Sep. 20, 2022

(65) Prior Publication Data

US 2023/0025774 A1    Jan. 26, 2023

Related U.S. Application Data

(63) Continuation of application No. PCT/CN2021/081591, filed on Mar. 18, 2021.

(30) Foreign Application Priority Data

Mar. 20, 2020 (CN) .......................... 202010205925.5
Mar. 20, 2020 (CN) .......................... 202020370900.6

(51) Int. Cl.
    *A61B 17/04* (2006.01)
(52) U.S. Cl.
    CPC ...... *A61B 17/0469* (2013.01); *A61B 17/0467* (2013.01); *A61B 17/0482* (2013.01);
    (Continued)
(58) Field of Classification Search
    CPC ............ A61B 17/0469; A61B 17/0467; A61B 2017/0488; A61B 17/0487;
    (Continued)

(56) References Cited

U.S. PATENT DOCUMENTS

| 7,235,086 B2 | 6/2007 | Sauer et al. |
| 2003/0204205 A1 | 10/2003 | Sauer et al. |

(Continued)

FOREIGN PATENT DOCUMENTS

| CN | 105916452 A | 8/2016 |
| CN | 106073836 A | 11/2016 |

(Continued)

OTHER PUBLICATIONS

The Extended European Search Report issued in corresponding EP Application No. EP21771267.8, mailed Jul. 18, 2023.

(Continued)

*Primary Examiner* — Katherine M Shi

(57) ABSTRACT

A forward-pushing release type suture locking device configured to fix a suture in a locking pin includes a collet and a thrust rod assembly sleeved outside the collet. The thrust rod assembly includes a thrust rod. A recessed portion is arranged at the thrust rod, and a protruding portion corresponding to the recessed portion is arranged at the collet. In a process that the thrust rod continuously moves distally in an axial direction, the thrust rod first pushes against a gradually raised side of the protruded portion, so as to allow the collet to deform to compress the locking pin, and allow the locking pin compressed by the collet to deform and fix the suture; and then the protruding portion is gradually accommodated in the recessed portion, so that at least part of deformations of the collet is restored to release the locking pin.

20 Claims, 17 Drawing Sheets

(52) U.S. Cl.
CPC .. *A61B 17/0487* (2013.01); *A61B 2017/0474* (2013.01); *A61B 2017/0488* (2013.01)

(58) Field of Classification Search
CPC ...... A61B 17/0401; A61B 2017/00243; A61B 2017/0496; A61B 17/0482; A61B 2017/0474; A61B 2017/0454
See application file for complete search history.

(56) References Cited

U.S. PATENT DOCUMENTS

| | | | |
|---|---|---|---|
| 2011/0251641 | A1 | 10/2011 | Sauer et al. |
| 2018/0256159 | A1 | 9/2018 | Sauer et al. |

FOREIGN PATENT DOCUMENTS

| | | |
|---|---|---|
| CN | 107920814 A | 4/2018 |
| CN | 209107426 U | 7/2019 |
| CN | 209186798 U | 8/2019 |
| CN | 212490016 U | 2/2021 |
| CN | 212630823 U | 3/2021 |

OTHER PUBLICATIONS

International Search Report issued in corresponding International Application No. PCT/CN2021/081591, mailed Jun. 21, 2021.

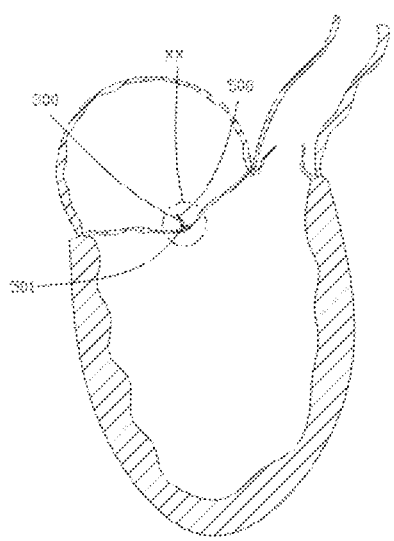
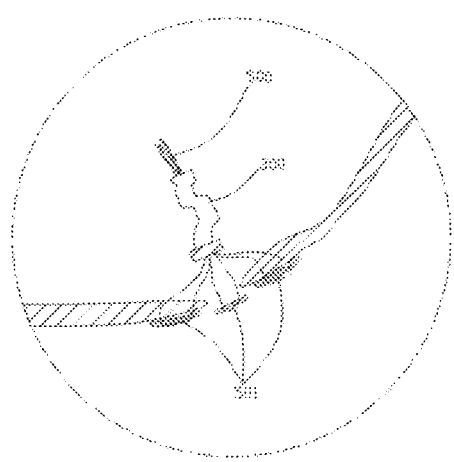
FIG. 19
FIG. 20

FORWARD-PUSHING FOR RELEASING SUTURE LOCKING DEVICE

CROSS-REFERENCE TO RELATED APPLICATION

The present disclosure is a continuation of International Disclosure No. PCT/CN2021/081591, filed on Mar. 18, 2021, which claims priority to and the benefit of Chinese Application patent Ser. No. 202010205925.5 and No. 202020370900.6, filed on Mar. 20, 2020. The disclosures of the aforementioned disclosures are hereby incorporated by reference in their entireties.

TECHNICAL FIELD

The present disclosure relates to the technical field of medical instruments, in particular to a forward-pushing release type suture locking device.

BACKGROUND

The operation step of knotting and fixing the suture is often required in the operation. Traditional surgery is operated under the condition of direct vision, and it can usually be knotted manually by the doctor. However, with the advancement of technology, various minimally invasive surgery and interventional surgery are becoming more common, such as endoscopic surgery, transcatheter interventional surgery, etc., such surgery only needs to cut a smaller operating window on the patient's body, through which instruments such as endoscopes or interventional catheters extend into the patient's body and reach a predetermined location for treatment. In this type of surgery, if the suture in the patient's body needs to be knotted or fixed, the operator usually needs to perform an operation outside the patient's body through the smaller operation window to knot the suture in the patient's body, which requires the use of suture locking devices.

In a related art, the suture locking device includes a locking pin with a hollow inner cavity, a collet matched with the locking pin and applying pressure on the locking pin to force it to deform, and a thrust rod connected to the collet and providing a driving force for the collet. A suture is passed through the hollow cavity of the locking pin, and the thrust rod is pushed forward toward a distal end of the collet in an axial direction to drive the collet to press the locking pin to fix the suture. After the locking pin is compressed, the thrust rod is pulled back toward a proximal end of the collet in the axial direction, so that the thrust rod is gradually away from the collet to release the force of the thrust rod on the collet, which allows the collet to release the locking pin. As illustrated in FIG. 1, since the thrust rod is driven to allow a direction of a force on the locking pin compressed by the collet to be opposite to that of the collet releasing the locking pin, a force curve of the thrust rod shows a cliff-jumping change in positive and negative directions, and a force curve of the collet also shows the cliff-like jump change in the positive and negative directions. When the thrust rod is pulled back and the locking pin is released from the collet, the thrust rod will drive the collet and the locking pin to jump violently, which will vigorously tear a sutured tissue, which is at a higher risk of being torn.

SUMMARY

Based on this, the present disclosure aims to provide a forward-pushing release type suture locking device for overcoming defects of the related art, which can avoid the severe jumping at a moment when a collet releases a locking pin, and can effectively reduce the risk of tissue being torn.

In order to solve the above technical problem, the present disclosure provides a forward-pushing release type suture locking device, which is configured to fix a suture in a locking pin. The forward-pushing release type suture locking device includes a collet and a thrust rod assembly sleeved outside the collet. The locking pin is accommodated at a distal end of the collet, and the collet is elastic. The thrust rod assembly includes a thrust rod. A recessed portion is arranged at a side of the thrust rod faced toward the collet, and a protruding portion corresponding to the recessed portion is arranged at a side of the collet faced toward the thrust rod. In a process that the thrust rod continuously moves distally in an axial direction, the thrust rod first pushes against a gradually raised side of the protruded portion, so as to allow the collet to deform to compress the locking pin, and allow the locking pin compressed by the collet to deform and fix the suture; and then the protruding portion is gradually accommodated in the recessed portion, so that at least part of deformations of the collet is restored to release the locking pin.

According to the forward-pushing release type suture locking device provided by the present disclosure, the recessed portion is arranged at the thrust, and the protruding portion is arranged at the collet. In the process that the thrust rod continuously moves towards the distal end in the axial direction, the thrust rod first pushes against the gradually raised side of the protruded portion, so as to allow the collet to deform to compress the locking pin, and allow the locking pin compressed by the collet to deform and fix the suture; and then the protruding portion is gradually accommodated in the recessed portion, so that at least part of deformations of the collet is restored to release the locking pin. That is, the locking pin being compressed and being released is achieved by continuously pushing the thrust rod, such that a continuity of forces of the thrust rod and the collet can be ensured by pushing the thrust rod in the whole process, which can avoid the severe jumping at a moment when the collet releases the locking pin, and can effectively reduce the risk of tissue being torn.

BRIEF DESCRIPTION OF THE DRAWINGS

In order to describe the technical solutions in the present disclosure more clearly, the accompanying drawings required to be used in the implementations will be simply introduced below. It is apparent that the accompanying drawings in the following descriptions are only some implementations of the present disclosure. Those of ordinary skill in the art may further obtain other apparent variations according to these accompanying drawings without creative work.

FIGS. 17-19 are schematic diagrams showing a repair process for the diseased tricuspid valve, which is carried out by a forward-pushing release type suture locking device provided by a first implementation of the present disclosure.

FIG. 20 is an enlarged view of part XX in FIG. 19.

DETAILED DESCRIPTION

Figure 1:
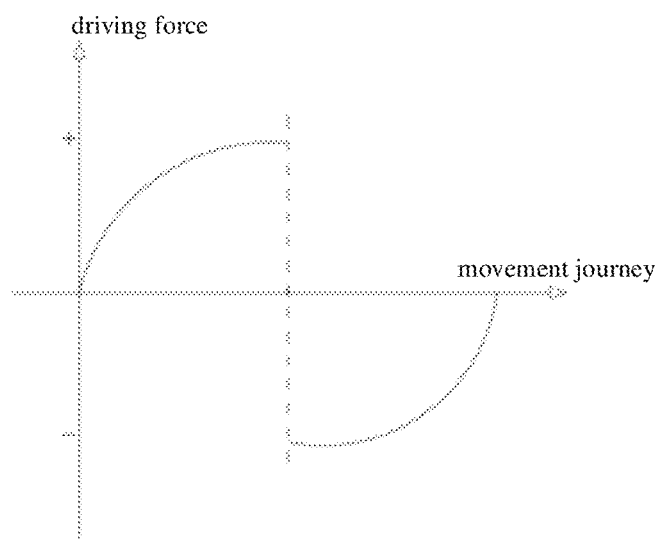
FIG. 1 is a schematic diagram of a relationship between a driving force and a movement journey of a thrust rod during a process that a collet compresses and releases a locking pin in a related art.

The technical solutions in the implementations of the present disclosure are clearly and completely described in the following in conjunction with the accompanying drawings of the present disclosure. It is apparent that the described implementations are only part of the implementations of the present disclosure, not all of the implementations. On the basis of the implementations of the present disclosure, all other implementations obtained on the premise of no creative work of those of ordinary skill in the art shall fall within the scope of protection of the present disclosure.

In the description of the present disclosure, it should be noted that an orientation or position relationship indicated by terms, such as "up", "down", "inner", and "outer", is based on an orientation or position relationship shown in the accompanying drawings. The terms are only used for the convenience of describing the application and simplifying the description instead of indicating or implying that the device or element must have a specific orientation or must be constructed and operated in a specific orientation, and thus cannot be interpreted as limitation to the present disclosure. Furthermore, terms, such as "first" and "second" are used herein for purposes of description and are not intended to indicate or imply relative importance or significance.

In order to describe a structure of a forward-pushing release type suture locking device more clearly, the defined terms, such as "proximal end", "distal end", "axial direction", and "radial direction" described in the present disclosure are commonly used terms in the field of interventional medicine. Specifically, during an operation, one end close to an operator is referred to as the "proximal end", and one end away from the operator is referred to as the "distal end". In the present disclosure, the proximal end is closer to the operator (surgeon) than the distal end. After assembling the device, each component thereof includes a proximal end and a distal end, and the proximal end of each component is closer to the operator than the distal end. The "axial direction" indicates a direction of a central axis of the device, and the "radial direction" indicates a direction perpendicular to the central axis. Unless otherwise defined, all technical and scientific terms used in the present disclosure have the same meaning as commonly understood by one of ordinary skill in the technical field to which the present disclosure belongs. The common terms used in the specification of the present disclosure are only for the purpose of describing specific implementations, and should not be intended to limit the present disclosure.

It should be noted that, when an element is referred to as being "arranged on" an another element, the element can be directly connected to the another element or indirectly connected to the another element through one or more connecting elements. When an element is referred to as being "connected to" an another element, the element can be directly connected to the another element or connected to the another element through one or more connecting elements.

Figure 2:
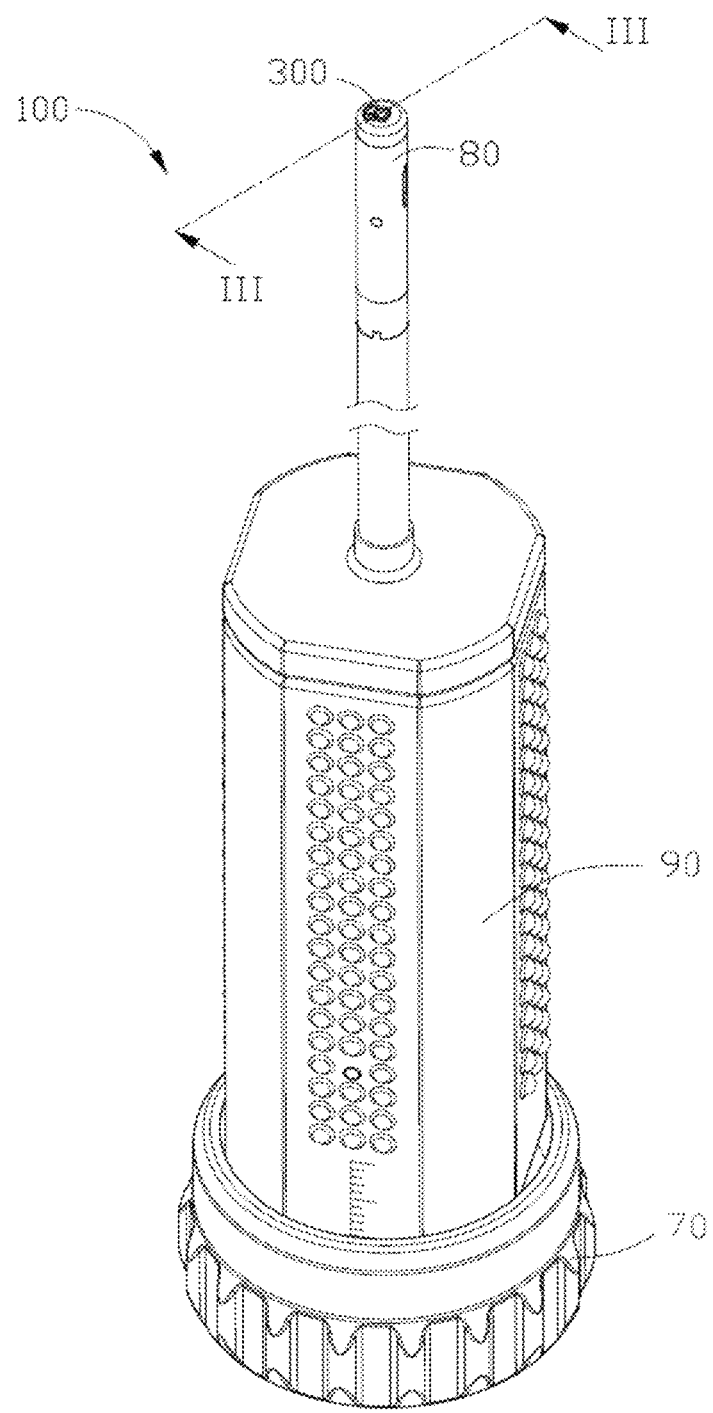
FIG. 2 is a schematic structural view of a forward-pushing release type suture locking device provided by a first implementation of the present disclosure.
Figure 3:
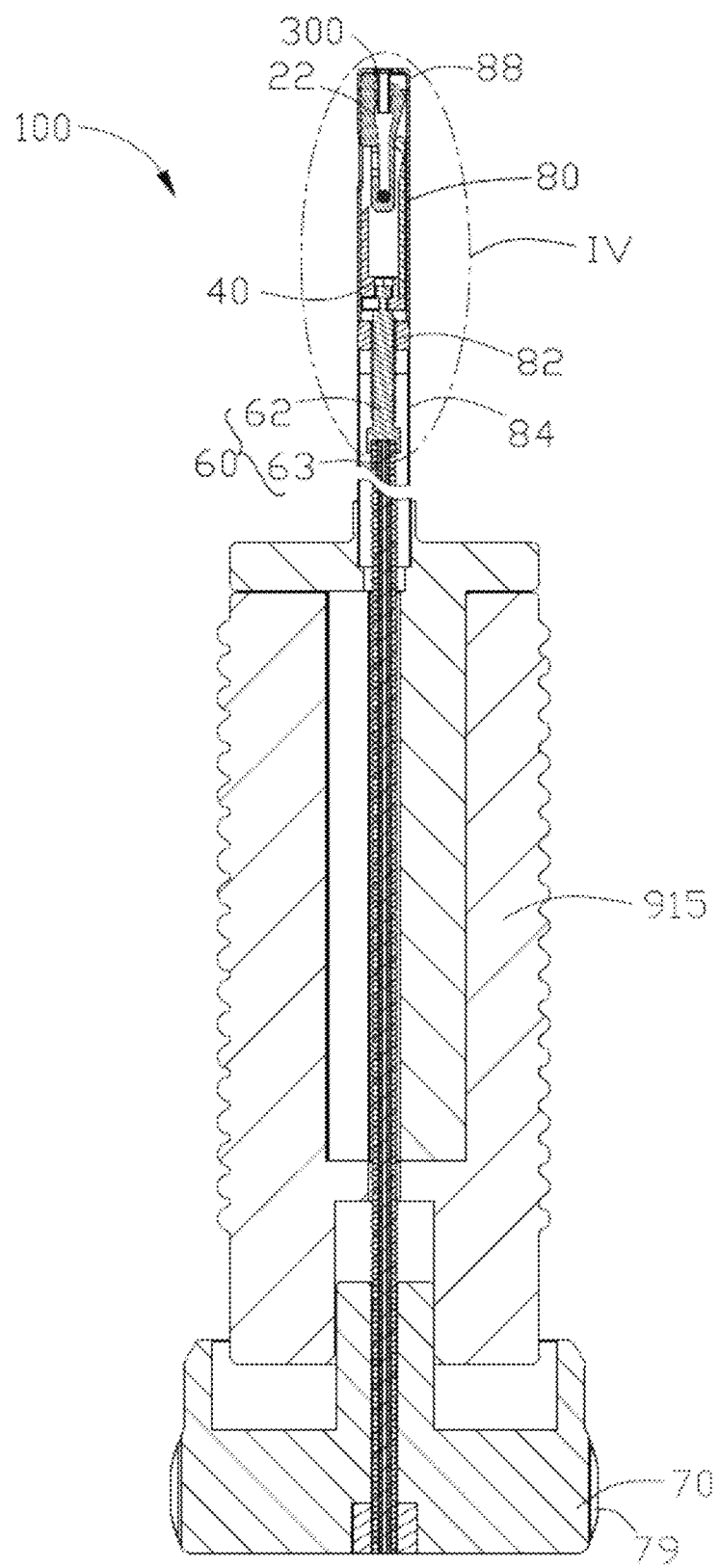
FIG. 3 is a cross-sectional view of FIG. 2 taken along line III-III.
Figure 4:
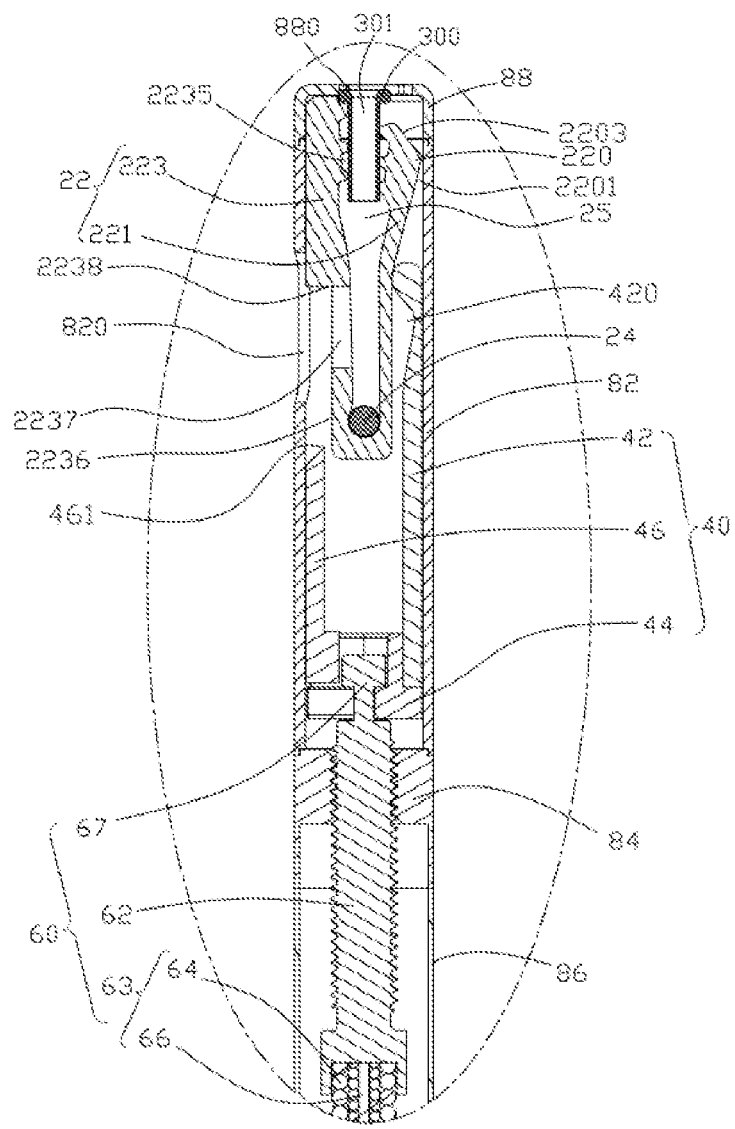
FIG. 4 is an enlarged view of part IV in FIG. 3.
Figure 8:
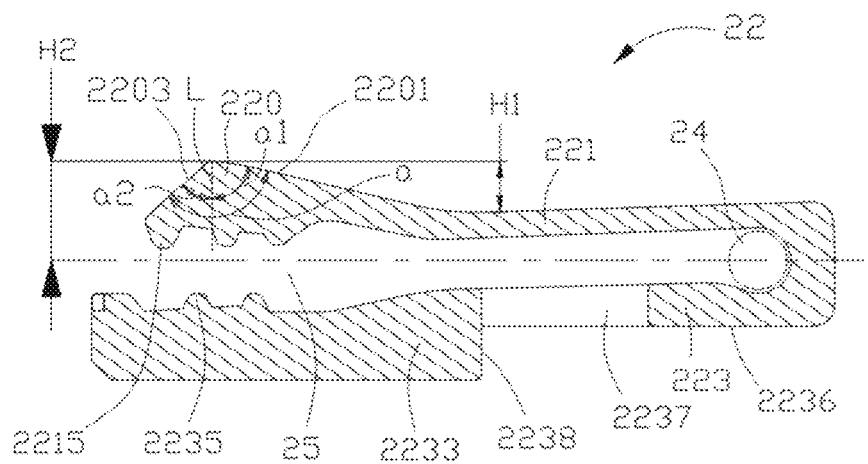
FIG. 8 is a cross-sectional view of a collet of the forward-pushing release type suture locking device in FIG. 4.

As illustrated in FIG. 2 to FIG. 4, a first implementation of the present disclosure provides a forward-pushing release type suture locking device 100, which is configured to fix a suture in a locking pin 300. The forward-pushing release type suture locking device 100 includes a collet 22 arranged at a distal end and configured to compress the locking pin 300 to deform, and a thrust rod assembly 40 sleeved outside the collet 22 and configured to open and close the collet 22, a transmission assembly 60 coupled to the thrust rod assembly 40, a driving member 70, an outer sleeve assembly 80 surrounding the collet 22, the thrust rod assembly 40, and the transmission assembly 60, and a handle 90 arranged at a proximal end. A distal end of the collet 22 is provided with a gap 25 for placing the locking pin 300 (as shown in FIG. 8). The locking pin 300 is provided with a threading cavity 301 along an axial direction, and the threading cavity 301 is configured to thread the suture. The thrust rod assembly 40 includes a thrust rod 42 arranged outside the collet 22. A recessed portion 420 is arranged at a side of the thrust rod 42 facing toward the collet 22. The collet 22 is fixed at an axial position, and the collet 22 is elastic. A protruding portion 220 corresponding to the recessed portion 420 is arranged at a side of the collet 22 faced toward the thrust rod 42. The transmission assembly 60 includes a thread transmission member 62 and a flexible inner core 63 with a certain axial length that is fixedly coupled to the thread transmission member 62. A distal end of the thread transmission member 62 is coupled to the thrust rod assembly 40.

The flexible inner core 63 rotates to drive the thread transmission member 62 to rotate, and the thread transmission member 62 rotates to drive the thrust rod assembly 40 to move axially toward the distal end, so that the thrust rod 42 moves toward the distal end in the axial direction to push against a gradually raised side of the protruding portion 220 of the collet 22, which allows the collet 22 to deform to compress the locking pin 300, and allow the locking pin 300 compressed by the collet 22 to deform and fix the suture. The flexible inner core 63 continuously rotates in the same direction to drive the thread transmission member 62 to rotate, and the thread transmission member 62 rotates to drive the thrust rod assembly 40 and the thrust rod 42 to move continuously towards the distal end in the axial direction, until the protruding portion 220 of the collet 22 is gradually accommodated in the recessed portion 420, so that at least part of deformations of the collet 22 is restored to release the locking pin 300.

Figure 24:
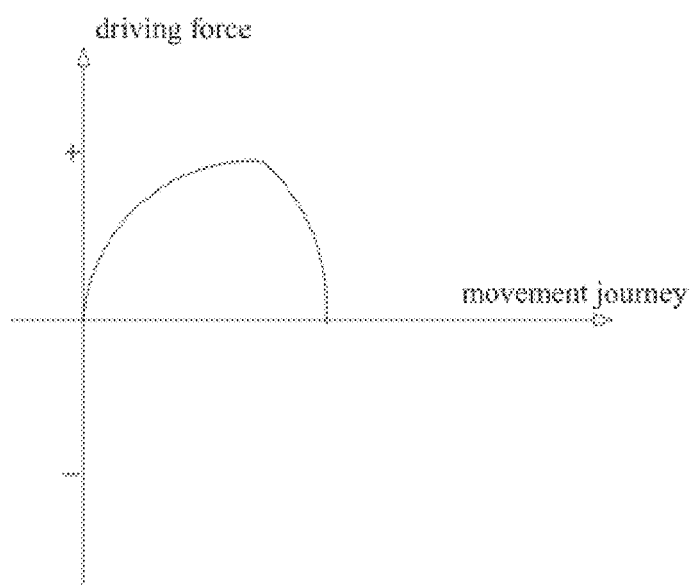
FIG. 24 is a schematic diagram showing a relationship between a driving force and a movement journey of the thrust rod during a process that a collet compresses and releases a locking pin in present disclosure.

According to the forward-pushing release type suture locking device 100 provided by the present disclosure, in the process of continuously pushing the thrust rod 42 distally in the axial direction, the thrust rod 42 first pushes against the gradually raised side of the protruding portion 220 of the collet 22, so as to allow the collet 22 to deform to compress the locking pin 300, and allow the locking pin 33 compressed by the collet 22 to deform and fix the suture; and then the protruding portion 220 is gradually accommodated in the recessed portion 420 of the thrust rod 42, so that at least part of deformations of the collet 22 is restored to release the locking pin 300. That is, the compressing and releasing of the locking pin 300 are carried out by continuously pushing the thrust rod 42, and the whole process of pushing ensures the continuity of the force on the thrust rod 42 and the collet 22 (as illustrated in FIG. 24), thus avoiding the severe jumping at a moment when the collet 22 releases the locking pin 300, preventing the collet 22 and the locking pin 300 from tearing the sutured tissue, such as valve leaflets, and thereby effectively reducing the risk of tissue being torn.

Furthermore, the thrust rod 42 is pushed distally in the axial direction to push against the gradually raised side of the protruding portion 220 of the collet 22. In the process of compressing the locking pin 300, resistance increases gradually, and a driving force required by the thrust rod 42 gradually increases accordingly. When the thrust rod 42 continuously moves distally in the axial direction and passes over the highest point of the protruding portion 220, the protruding portion 220 is gradually accommodated in the recessed portion 420, such that the resistance will gradually decrease, and the driving force required by the thrust rod 42 will gradually decrease accordingly. Therefore, the operator can know whether the locking pin 300 has been compressed and whether the suture has been fixed through the perception of the operating feel.

On the other hand, the forward-pushing release type suture locking device 100 converts rotation torque of the flexible inner core 63 and the thread transmission member 62 into axial thrust by which the thread transmission member 62 drives the thrust rod 42 to move in the axial direction, so as to drive the thrust rod 42 to move toward the distal end in the axial direction. Since the thread transmission member 62 is rigid and has a short length, the thrust loss is extremely small, and the thrust can be smoothly and effectively transmitted to the thrust rod 42 to push against the collet 22, such that the collet 22 can effectively compress the locking pin 300 to allow the locking pin 300 to be sufficiently deformed, which ensures that the suture is securely fixed by the locking pin 300.

As illustrated in FIG. 3 and FIG. 4, the outer sleeve assembly 80 includes a sleeve 82 for accommodating the collet 22 and the thrust rod assembly 40, an end cover 88 fixed to a distal end of the sleeve 82, a connection sleeve 84 fixed to a proximal end of the sleeve 82, and a flexible outer tube 86 fixed to a proximal end of the connection sleeve 84. The thread transmission member 62 is rotatably coupled to the outer sleeve assembly 80. The thread transmission member 62 rotates relative to the outer sleeve assembly 80 to drive the thrust rod 42 to move in the axial direction. The collet 22 and the thrust rod assembly 40 are accommodated in the sleeve 82. The collet 22 is fixedly coupled to the sleeve 82 so as to fix the collet 22 at an axial position. The flexible outer tube 86 is sleeved outside the flexible inner core 63. The thread transmission member 62 is rotatably coupled in the connection sleeve 84. Specifically, the thread transmission member 62 and the connection sleeve 84 are driven through threaded cooperation. In the embodiment, the thread transmission member 62 is a transmission screw rod, and a connection portion 67 is arranged at a distal end of the thread transmission member 62. The connection portion 67 is rotatably coupled to the thrust rod assembly 40. The thread transmission member 62 moves in the axial direction while rotates to drive the thrust rod assembly 40 to move in the axial direction.

As illustrated in FIG. 4, a distal end of the flexible outer tube 86 is fixedly coupled to a proximal end of the connection sleeve 84. The connection sleeve 84 is fixedly coupled between the sleeve 82 and the flexible outer tube 86. A proximal end of the flexible outer tube 86 is fixedly coupled to a distal end of the handle 90. An inner cavity of the flexible outer tube 86 is in air communication with an inner cavity of the connection sleeve 84, and the connection sleeve 84 is screwed with the thread transmission member 62. The flexible outer tube 86 is a tube body with a certain supporting force, which is preferably a laser-cut tube, or a tube body constructed as a spiral structure, a woven mesh structure, etc. In the embodiment, the flexible outer tube 86 adopts the laser-cut tube. The flexible outer tube 86 may be made of materials such as stainless steel, nickel-titanium alloy, or cobalt-chromium alloy. In the embodiment, the flexible outer tube 86 is made of the nickel-titanium alloy.

The sleeve 82 is a hollow tube. A proximal end of the sleeve 82 is clamped to a distal end of the connection sleeve 84. A distal end of the sleeve 82 is clamped to the end cap 88. A threading groove 820 is provided with a peripheral wall of the sleeve 82 adjacent to the collet 22. The threading groove 820 is configured for the suture passing through the locking pin 300 to pass out. A distal end of the end cover 88 is provided with a suture inlet 880 in air communication with an inner cavity of the sleeve 82, and the locking pin 300 is inserted into the inner cavity of the sleeve 82 through the suture inlet 880.

Figure 5:
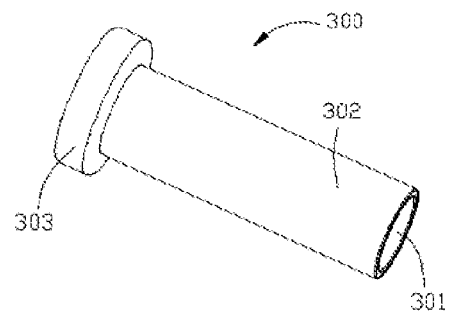
FIG. 5 is a schematic structural view of a locking pin compressed by a collet of a forward-pushing release type suture locking device provided by a first implementation of the present disclosure.
Figure 6:
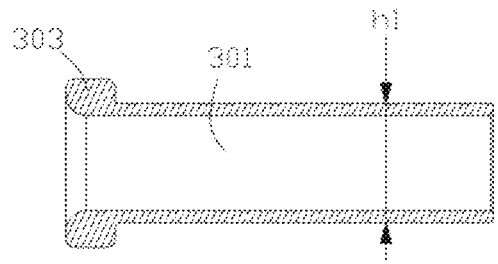
FIG. 6 is a cross-sectional view of the locking pin in FIG. 5.

As illustrated in FIG. 5 and FIG. 6, the locking pin 300 includes a locking cylinder 302 and a circular pad 303 arranged at a distal end of the locking cylinder 302. An outer diameter of the circular pad 303 of the locking pin 300 is larger than an outer diameter of the locking cylinder 302. The threading cavity 301 of the locking pin 300 passes through two opposite ends of the locking pin 300 in the axial direction. The threading cavity 301 is configured for accommodating and passing the suture. The locking cylinder 302 may be collapsed when subjected to an external mechanical force to fix the suture in the threading cavity 301 of the locking pin 300. The locking pin 300 may have various shapes, for example, a cylindrical shape, a prismatic shape, an oval shape, etc., as long as the locking pin 300 has the threading cavity 301 for accommodating the suture. A smooth transition is provided between a distal opening of the threading cavity 301 of the locking pin 300 and a distal surface of the locking pin 300, so as to avoid wearing the suture or scratching an internal tissue of the patient at a connection between the distal opening of the threading cavity 301 and the distal surface of the locking pin 300. The locking pin 300 is made of biocompatible materials, such as stainless steel, titanium, nickel-titanium alloy, cobalt-chromium alloy. The locking pin 300 is preferably made of the titanium or the stainless steel.

Figure 7:
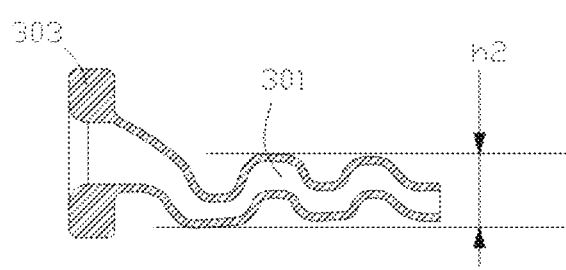
FIG. 7 is a cross-sectional view of the locking pin in FIG. 5 after being compressed.

In the embodiment, as illustrated in FIG. 6, when the locking pin 300 is not collapsed by external force, an initial height h1 at a middle of the locking pin 300 is equal to the outer diameter of the locking cylinder 302 of the locking pin 300. As illustrated in FIG. 7, when the locking cylinder 302 of the locking pin 300 is collapsed under an external mechanical force, the suture is fixed in the threading cavity 301 of the locking pin 300. At this time, a height h2 of the middle of the locking pin 300 after being collapsed is less than the initial height h1.

In order to improve a connection between the locked pin 300 after being compressed and the suture, an anti-slip structure can be arranged on an inner peripheral surface of the threading cavity 301. For example, an anti-slip texture is arranged on the inner peripheral surface of the threading cavity 301, or the inner peripheral surface of the threading cavity 301 is roughened. After the locking pin 300 is deformed under an external compressing force, friction between the suture and the inner peripheral surface of the threading cavity 301 increases, so that the suture is more firmly fixed in the threading cavity 301 of the locking pin 300.

Figure 9:
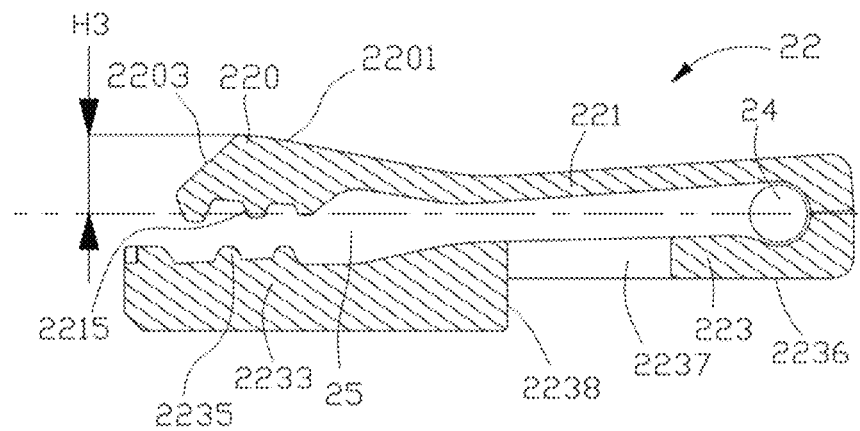
FIG. 9 is a schematic structural view of the collet in FIG. 8 being in a deformation state.

As illustrated in FIG. 8 and FIG. 9, the collet 22 includes a first clip 221 and a second clip 223, which are made in one piece and arranged opposite to each other. The protruding portion 220 is arranged on one side of the first clip 221 away from the second clip 223. A gap 25 is formed between the first clip 221 and the second clip 223. When the driving member 70 drives the thread transmission member 62 to rotate, the thread transmission member 62 moves axially while rotating and pushes the thrust rod 42 to move in the axial direction because the connection sleeve 84 is fixed in place. That is, the rotation of the thread transmission member 62 is converted into the axial movement of the thrust rod 42, such that the thrust rod 42 slides against the protruding portion 220 of the collet 22 to drive the first clip 221 and the second clip 223 to move toward each other and squeeze the locking pin 300, to allow the locking pin 300 to be deformed and fixing the suture.

In the embodiment, the first clip 221 and the second clip 223 are made in one piece by elastic hard materials. A proximal end of the collet 22 is closed. A pin 24 perpendicular to the axial direction passes through the proximal end of the collet 22. Two opposite ends of the pin 24 are respectively fixed to the sleeve 82. The pin 24 positions the collet 22, thus preventing the collet 22 from moving in the axial direction. A solid part which connected proximal ends of the first clip 221 and the second clip 223 provides supporting and driving forces for the first clip 221 to rebound.

In the embodiment, the protruding portion 220 is located at a distal end of the side of the first clip 221 away from the second clip 223. The protruding portion 220 includes a first outer slope 2201 and a second outer slope 2203 intersecting with the first outer slope 2201. The first outer slope 2201 and the second outer slope 2203 intersect at the side of the first clip 221 away from the second clip 223. The first outer slope 2201 gradually rises from a proximal end of the first outer slope 2201 to a distal end of the first outer slope 2201. The second outer slope 2203 gradually decreases from a proximal end of the second outer slope 2203 to a distal end of the second outer slope 2203. As illustrated in FIG. 4 and FIG. 9, the first outer slope 2201 corresponds to a side surface of the protruding portion 220 that is gradually raised in a radial direction from a proximal end to a distal end thereof. The distal end of the thrust rod 42 slides against the first outer slope 2201 in the axial direction to press the first outer slope 2201, so as to press the first clip 221 to gradually move closer to the second clip 223 to compress the locking pin 300. The thrust rod 42 continues to be pushed toward the distal end, until the protruding portion 220 is gradually accommodated in the recessed portion 420, such that the collet 22 rebounds, the first clip 221 is far away from the second clip 223, and the gap 25 between the first clip 221 and the second clip 223 is increased to be greater than the height h2 after collapsing the locking pin 300, which releases the locking pin 300. Furthermore, a side surface of a distal end of the first clip 221 facing toward the gap 25 is provided with a first tooth 2215. The first tooth 2215 includes a plurality of grooves. Each of plurality of grooves extends in a direction substantially perpendicular to the axial direction.

As illustrated in FIG. 8, the first outer slope 2201 is located at a proximal end of the protruding portion 220. The first outer slope 2201 gradually slopes toward a side far away from the second clip 223 from the proximal end of the first outer slope 2201 to the distal end of the first outer slope 2201. The second outer slope 2203 is located at a distal end of the protruding portion 220. The second outer slope 2203 gradually slopes toward a side close to the second clip 223 from the proximal end of the second outer slope 2203 to the distal end of the second outer slope 2203. An angle "a" is formed between the first outer slope 2201 and the second outer slope 2203 of the protruding portion 220, preferably, the angle "a" satisfies the following relation: $120°\leq"a"<180°$. Furthermore, when the collet 22 is in an initial state (or called a natural state, which refers to a state in which the thrust rod 42 does not push against the collet 22), a range of a first angle "a1" formed between the first outer slope 2201 and a vertical plane "L" perpendicular to the axial direction is greater than or equal to 70 degrees, and less than 90 degrees, and a range of a second angle "a2" formed between the second outer slope 2203 and the vertical plane "L" perpendicular to the axial direction is greater than or equal to 50 degrees and less than 90 degrees. The sum of the first angle "a1" and the second angle "a2" is equal to the angle "a" between the first outer slope 2201 and the second outer slope 2203. It should be noted that, "a2"<"a1", that is, an inclination of the first outer slope 2201 is less than an inclination of the second outer slope 2203. Since the inclination of the first outer slope 2201 is relatively gentle, the driving force for pushing the thrust rod 42 to push against and compress the collet 22 can be reduced, to allow the collet 22 to be gradually deformed.

As illustrated in FIG. 8, a height difference "H1" between the distal end and the proximal end of the first outer slope 2201 is greater than or equal to a diameter of a hole of defined inside the locking cylinder 302 of the locking pin 300, which is a diameter of the threading cavity 301, and is less than an outer diameter of the locking cylinder 302 of the locking pin 300. Therefore, when the thrust rod 42 pushes the distal end of the first outer slope 2201, the first clip 221 and the second clip 223 can sufficiently compress the locking pin 300 to fix the suture passing through the locking pin 300.

As illustrated in FIG. 8 and FIG. 9, a height difference "H" between the highest point of the protruding portion 220 before the deformation of the first clip 221 and that of the protruding portion 220 after the deformation and rebound is less than a difference between the initial height "h1" of the locking pin 300 and the height "h2" of the locking pin 300 after being collapsed. Specifically, a vertical length between the highest point of the protruding portion 220 before the deformation of the first clip 221 and an axial plane passing through an axis of the pin 24 is "H2" (as illustrated in FIG. 8). After the first clip 221 is compressed and rebounds, the protruding portion 220 is accommodated in the recessed portion 420 of the thrust rod 42. At this time, a vertical length between the highest point of the protruding portion 220 and the axial plane passing through the axis of the pin 24 is "H3" (as illustrated in FIG. 9). The height difference "H" is obtained by subtracting "H3" from "H2". The height difference H is less than a difference between the initial height "h1" of the locking pin 300 before being compressed and the height "h2" after the locking pin 300 being compressed, such that it is convenient for the locking pin 300 to fall off from the gap 25 of the collet 22 smoothly. When the difference "H" is 0, the first clip 221 is completely restored to the initial state.

A smooth transition is provided at an intersection between the first outer slope 2201 and the outer slope 2203, such that it is convenient for the thrust rod 42 to cross the intersection between the first outer slope 2201 and the outer slope 2203 smoothly, that is, it is convenient for the thrust rod 42 to slide from the first outer slope 2201 to the second outer slope 2203 smoothly.

A side surface of the second clip 223 facing toward the first clip 221 is provided with a second tooth 2235 adjacent to the distal end. The second tooth 2235 includes a plurality of grooves. An extension direction of each of plurality of grooves of the second tooth 2235 is the same as that of the first teeth 2215. When the first collect 221 and the second clip 223 are close to each other along the pin 24, the first teeth 2215 of the first clip 221 and the second teeth 2235 of the second clip 223 can be staggered and engaged with each other. Therefore, the first clip 221 is elastically deformed toward the second clip 223, and the locking pin 300 placed in the gap 25 is squeezed by the first teeth 2215 and the second teeth 2235 into a shape with curvature. A proximal end of a side surface of the second clip 223 away from the first clip 221 is provided with a guiding surface 2236 in horizontal direction. A threading hole 2237 in air communication with the gap 25 is formed on the guiding surface 2236, such that it is convenient for the suture after passing through the locking pin 300 to pass through the threading hole 2237. A positioning block 2233 protrudes from a distal end of the side surface of the second clip 223 away from the first clip 221. A proximal surface of the positioning block 2233 is close to the threading hole 2237, and the proximal surface of the positioning block 2233 is a plane for cutting suture (as cutting surface 2238).

Figure 10:
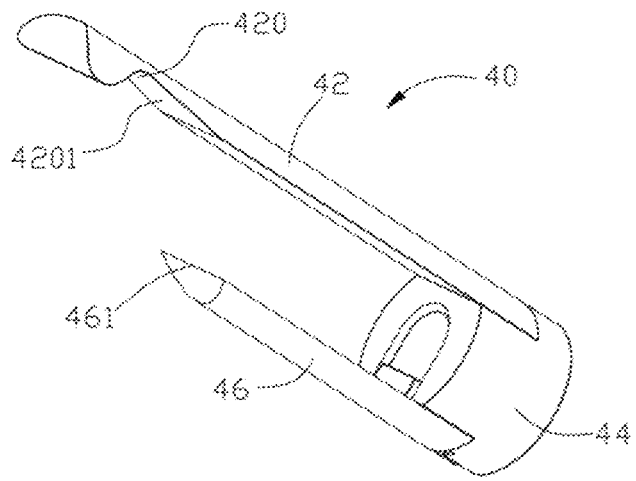
FIG. 10 is a schematic structural view of a thrust rod assembly of the forward-pushing release type suture locking device in FIG. 4.
Figure 11:
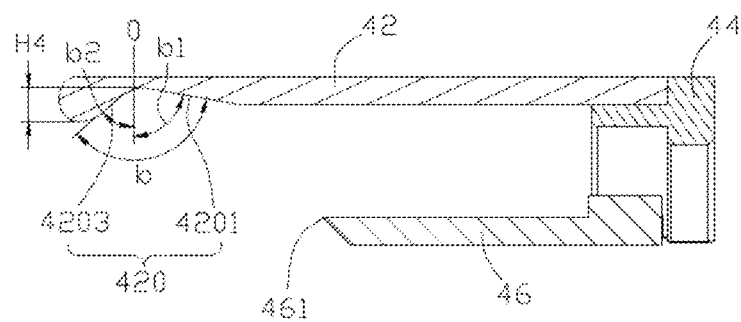
FIG. 11 is a cross-sectional view of the thrust rod assembly in FIG. 10.
Figure 12:
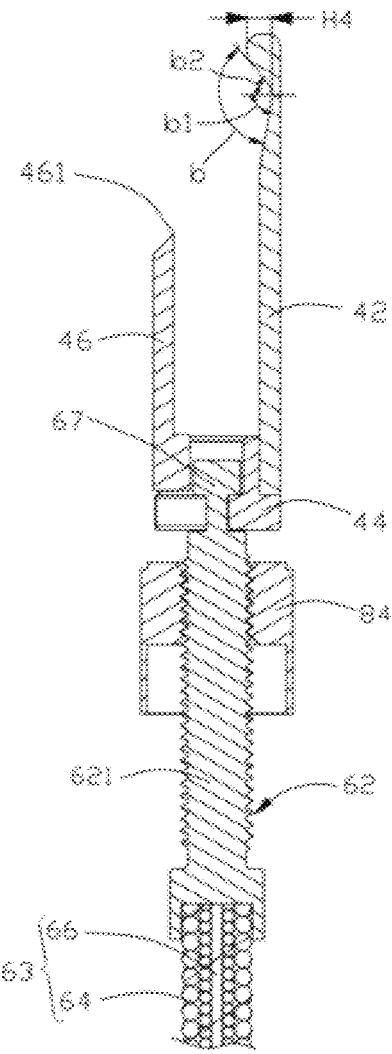
FIG. 12 is a cross-sectional view of a thrust rod assembly and a transmission assembly of the forward-pushing release type suture locking device in FIG. 2.

As illustrated in FIG. 4 and FIG. 10 to FIG. 11, the thrust rod assembly 40 also includes a pedestal 44 movably mounted in the sleeve 82 along the axial direction and a cutting member 46. The cutting member 46 is fixedly coupled to one side of the pedestal 44, and the proximal end of the thrust rod 42 is fixedly coupled to an another side of the pedestal 44 opposite to the cutting member 46. The thrust rod 42 extends toward the distal end in the axial direction. The connection portion 67 is rotatably coupled to the pedestal 44, and an axial limiting structure is provided between the connection portion 67 and the pedestal 44. The cutting member 46 and the thrust rod 42 are opposite to and spaced apart from each other. The cutting member 46 slides on the guiding surface 2236 in the axial direction.

The recessed portion 420 is provided on a side of the thrust rod 42 fitted to the first clip 221 and is close to the distal end of the thrust rod 42. The recessed portion 420 includes a first inner slope 4201 and a second inner slope 4203 intersecting with the first inner slope 4201. The first inner slope 4201 is farther from the distal end of the thrust rod 42 than the second inner slope 4203. When the protruding portion 220 is accommodated in the recessed portion 420, the first outer slope 2201 corresponds to the first inner slope 4201, and the second outer slope 2203 corresponds to the second inner slope 4203.

As illustrated in FIG. 11, the first inner slope 4201 gradually slopes toward a side far away from the first clip 221 from a proximal end of the first inner slope 4201 to a distal end of the first inner slope 4201, and the second inner slope 4203 gradually slopes toward a side close to the first clip 221 from a proximal end of the second inner slope 4203 to a distal end of the second inner slope 4203. An arc transition is provided at an edge of the distal end of the second outer slope 4203, such that it is convenient for the thrust rod 42 to smoothly slide against the second outer slope 2203. An arc transition is provided between a distal surface of the thrust pod 42 and a surface of the thrust pod 42 fitted to collet 22, such that it is convenient for the thrust rod 42 to smoothly slide against the first outer slope 2201.

An angle "b" formed between the first inner slope 4201 and the second inner slope 4203 of the recessed portion 420 is greater than or equal to the angle "a" between the first outer slope 2201 and the second outer slope 2203 of the protruding portion 220, so as to allow the protruding portion 220 to be accommodated in the recessed portion 420. Preferably, a third angle "b1" formed between the first inner slope 4201 and a vertical surface "O" perpendicular to the axial direction is greater than or equal to the first angle "a1". A fourth angle "b2" formed between the second inner slope 4203 and the vertical surface "O" perpendicular to the axial direction is greater than or equal to the second angle "a2". The sum of the third angle "b1" and the fourth angle "b2" is equal to the angle "b" formed between the first inner slope 4201 and the second inner slope 4203.

As illustrated in FIG. 11, a maximum depth "H4" of the recessed portion 420 is a vertical length from the highest point of the recessed portion 420 to the surface of the thrust rod 42 fitted to the collet 22. The maximum depth "H4" is greater than or equal to the height difference "H1" formed between the distal end and the proximal end of the first outer slope 2201, which is a maximum height of the protruding portion 220, so as to ensure that the protruding portion 220 can be completely accommodated in the recessed portion 420, and provide a sufficient rebound space for the collet 22. When the protruding portion 220 is accommodated in the recessed portion 420, a height of the gap 25 is greater than the height "h2" of the locking pin 300 after being collapsed, so as to facilitate the release of the locking pin 300.

A distal end of the cutting member 46 is provided with a blade 461. When the protruding portion 220 is completely accommodated in the recessed portion 420, the blade 461 abuts against the cutting surface 2238 to cut the suture passing through the threading hole 2237.

It will be appreciated that, in other embodiments, the protruding portion 220 can also be a protrusion having a shape, such as a hemisphere shape, a circular truncated cone shape, a cone shape. The recessed portion 420 can also be a groove or an opening, which is adapted to the protruding portion 220 having the shape, such as the hemisphere shape, the circular truncated cone shape, the cone shape.

As illustrated in FIG. 3, FIG. 4, and FIG. 12 to FIG. 14, the flexible inner core 63 includes a flexible inner tube 64 coupled to a proximal end of the thread transmission member 62 and a mandrel 66 inserted into an inner cavity of the flexible inner tube 64. The connection portion 67 is coupled between a distal end of the thread transmission member 62 and the pedestal 44 of the thrust rod assembly 40. The flexible inner tube 64 is wound on the mandrel 66. The flexible inner tube 64 and the mandrel 66 together constitute the flexible inner core 63. The thread transmission member 62 includes a transmission screw rod 621. The transmission screw rod 621 is screwed to an inner thread of the connection sleeve 84. A distal end of the flexible inner tube 64 is fixedly coupled to the thread transmission member 62, and a proximal end of the flexible inner tube 64 is fixedly coupled to the driving member 70 for driving the flexible inner core 63 and the thread transmission member 62 to rotate. The flexible inner tube 64 is a tube body with a certain supporting force, which is preferably a tube body constructed as a spiral structure, a woven mesh structure, etc. The flexible inner tube 64 can be made of materials such as stainless steel, nickel-titanium alloy, or cobalt-chromium alloy. An outer diameter of the flexible inner tube 64 is less than an inner diameter of the flexible outer tube 86. The flexible inner tube 64 is rotatable relative to the connection sleeve 84 to drive the thread transmission member 62 to rotate and move in the axial direction.

The mandrel 66 is inserted into an inner cavity of the flexible inner tube 64. The mandrel 66 has some flexibility. Preferably, the mandrel 66 can be made of materials such as stainless steel, nickel-titanium alloy, cobalt-chromium alloy. The mandrel 66 is provided, thus facilitating the winding of a wire on the mandrel 66 to form the flexible inner tube 64, and thereby enhancing the twist control of the flexible inner core 63.

The transmission screw rod 621 rotates and moves along the axial direction to drive the connection portion 67 to rotate relative to the pedestal 44, and at the same time, the distal end of the transmission screw rod 621 pushes against the pedestal 44, the thrust rod 42 and the cutting member 46 along the axial direction to move distally.

In other embodiments, the connection portion 67 can also be fixedly coupled to the thrust rod assembly 40. The connection portion 67 is rotatably coupled with the thread transmission member 62. A limiting structure, which is configured to prevent the connection portion 67 from moving relatively to the thread transmission member 62 in the axial direction, is arranged between the connection portion 67 and the thread transmission member 62, to allow the connection portion 67 to be rotatably coupled to the thread transmission member 62.

Figure 13:
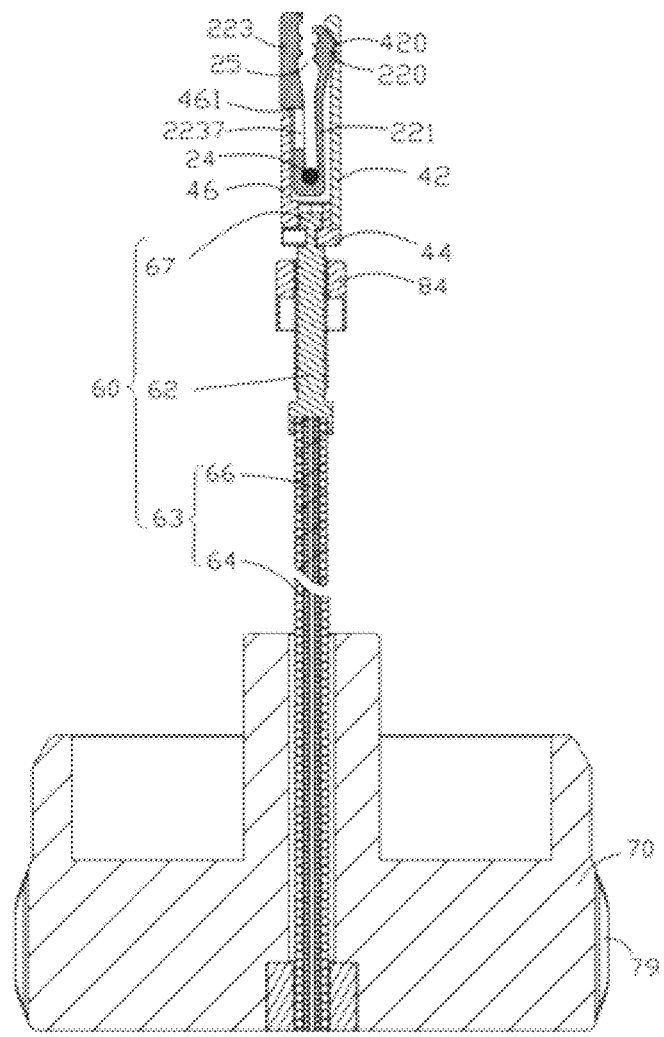
FIG. 13 is a cross-sectional view of a collet, a thrust rod assembly, a transmission assembly, and a driving member of the forward-pushing release type suture locking device in FIG. 2.
Figure 14:
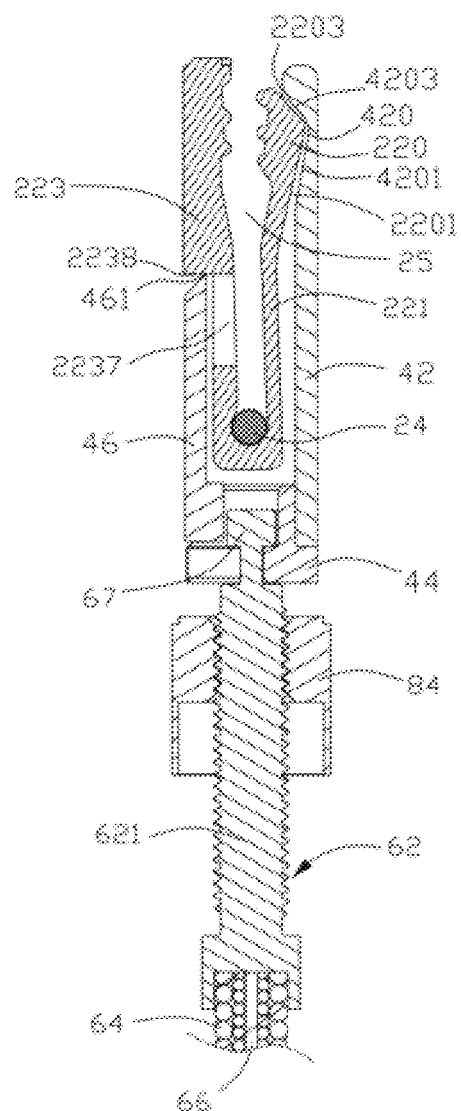
FIG. 14 is an enlarged view of the collet, the thrust rod assembly, and part transmission assembly in FIG. 13.
Figure 15:
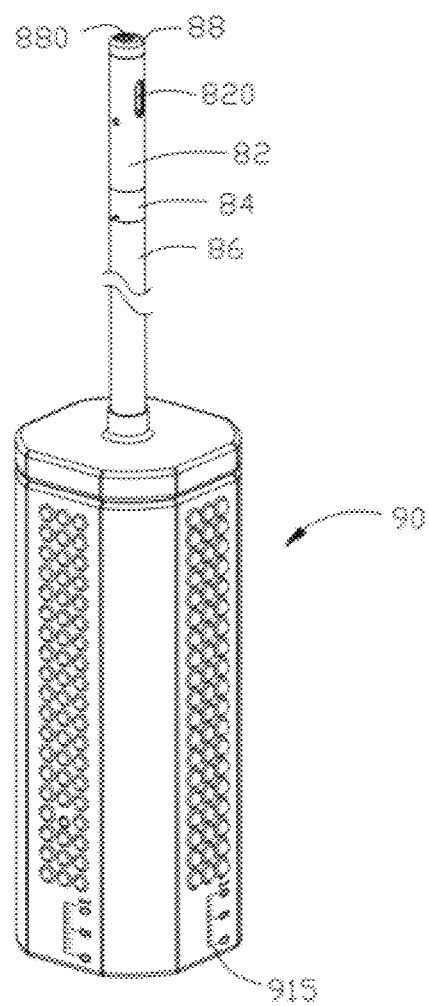
FIG. 15 is a schematic structural view of a handle and an outer sleeve assembly of the forward-pushing release type suture locking device in FIG. 2.
Figure 16:
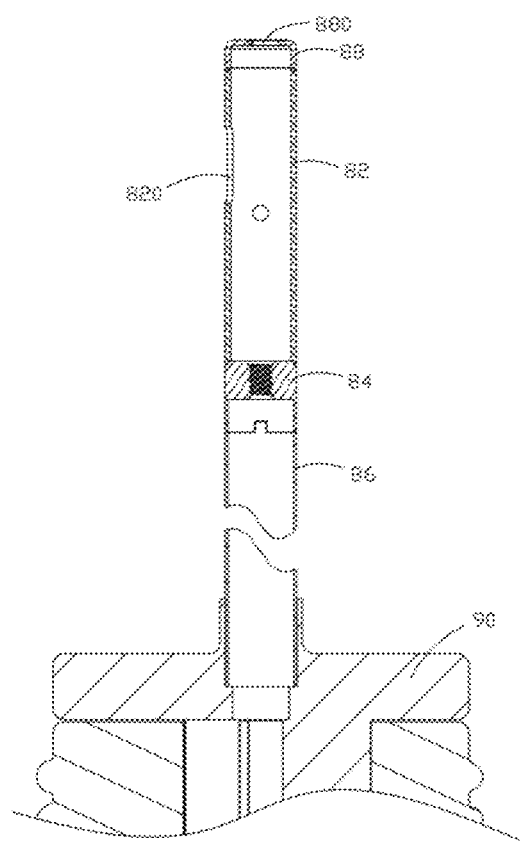
FIG. 16 is a schematic structural view of part handle and the outer sleeve assembly in FIG. 15.

As illustrated in FIG. 3 and FIG. 13, the driving member 70 is coupled to a proximal end of the transmission assembly 60. Specifically, the driving member 70 is a rotating member rotatably arranged at a proximal end of the handle 90. The proximal ends of the flexible inner tube 64 and the mandrel 66 are fixedly coupled to the driving member 70. The driving member 70 rotates to drive the flexible inner tube 64 and the mandrel 66 to rotate together. An anti-slip mechanism 79 is arranged on an outer wall of the driving member 70, so as to facilitate the rotation of the driving member 70 by holding the anti-slip mechanism 79.

As illustrated in FIG. 2, FIG. 3, FIG. 15, and FIG. 16, the driving member 70 is rotatably coupled to the proximal end of the handle 90. At least one length scale 915 is arranged on the handle 90 adjacent to the driving member 70 in the axial direction. The at least one length scale 915 is configured to display displacement of the driving member 70 moving in the axial movement. When a distal surface of the driving member 70 faces "0" on the length scale 915, the first clip 221 and the second clip 223 of the collet 22 are in a fully opened state, and the thrust rod 42 does not apply a pushing force on the collet 22 in the axial direction. When the driving member 70 rotates and moves in the axial direction to a point where the distal surface of the driving member 70 faces a certain scale value such as "6" on the length scale 915, the thrust rod 42 pushes against the highest point of the protruding portion 220 of the collet 22, the first clip 221 and the second clip 223 compress the locking pin 300 to deform and fix the suture passing through the locking pin 300. When the driving member 70 continues to rotate in the same direction and moves in the axial direction to a point where the distal surface of the driving member 70 faces an another scale value, such as "7.5", on the length scale 915, the protruding portion 220 of the collet 22 is accommodated in the recessed portion 420 of the thrust rod 42, and at least part of deformations of the first clip 223 of the collet 22 is restored, which facilitates the release of the locking pin 300.

As illustrated in FIG. 17 to FIG. 23, the following takes a tricuspid valve repair operation as an example to illustrate applications of the forward-pushing release type suture locking device 100 provided by the disclosure.

The tricuspid valve is a one-way "valve" between a right atrium (RA for short) and a right ventricle (RV for short), which can ensure blood flow from the RA to the RV. A normal healthy tricuspid valve has several chordae tendineae. The leaflets of the tricuspid valve include the anterior leaflet, the posterior leaflet, and the septal leaflet. When the RV is in a diastolic state, the anterior leaflet, the posterior leaflet, and the septal leaflet are apart from each other, and the blood flows from the RA to the RV. When the RV is in a systole state, the chordae tendineae is stretched to prevent the leaflets from being pushed by the blood flows to the RA, and the anterior leaflet, the posterior leaflet, and the septal leaflet are in a good close state to ensure the blood flows from the RV to the pulmonary artery through the pulmonary valve (PV for short). Different from the tricuspid valve in the health state, under the condition that the tricuspid valve has lesions, the tricuspid valve cannot return to a sufficient close state, but the tricuspid valve cannot close sufficiently when the RV is in the systole state, and the momentum of the blood flows can further cause the leaflets to fall into the RA, thereby resulting in blood regurgitation, called "tricuspid regurgitation". For tricuspid regurgitation, by adopting an interventional operation, sutures are implanted into at least one leaflet, and then the sutures on different leaflets are fixed together, which is carried out by the locking device in the present disclosure, so as to perform an edge-to-edge repair process. Specifically, the process includes as follows.

Figure 17:
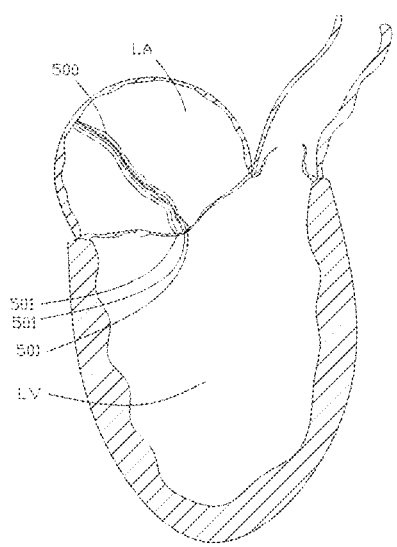

At step 1, as illustrated in FIG. 17, a plurality of sutures 500 with elastic pads 501 are first implanted to the anterior leaflet, the posterior leaflet, and the septal leaflet of the tricuspid valve on a patient, respectively. A point contact between the suture 500 and the leaflets is converted to a surface contact between the elastic pads 501 and the leaflets, so that the risk of leaflet being torn may be reduced effectively.

Figure 21:
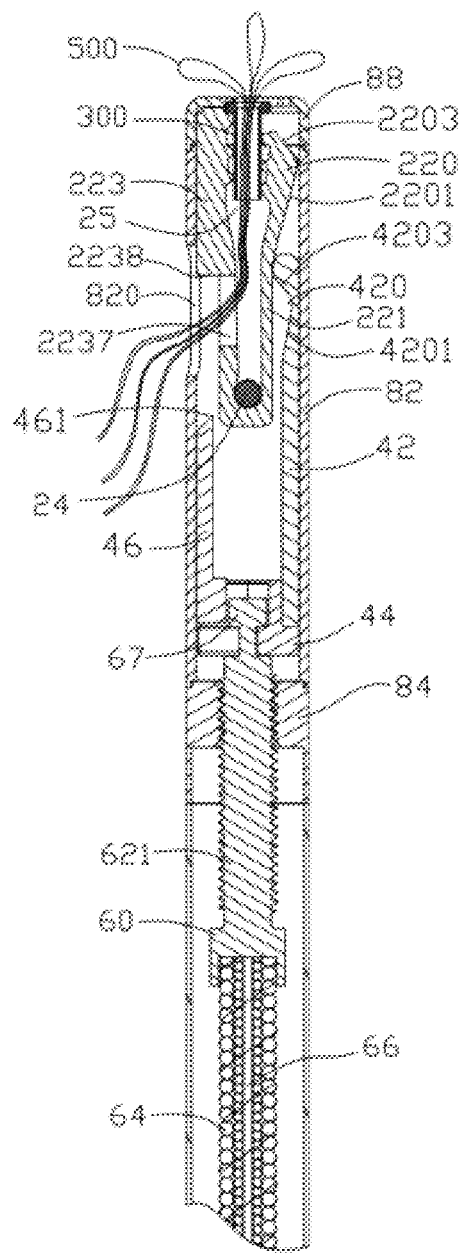
FIGS. 21-23 are schematic diagrams showing a process for fixing a suture in the locking pin, which is carried out by a forward-pushing release type suture locking device provided by a first implementation of the present disclosure.

At step 2, as illustrated in FIG. 17 and FIG. 21, the plurality of sutures 500 on two or three leaflets are inserted into the threading cavity 301 of the locking pin 300 of the forward-pushing release type suture locking device 100 outside the patient, and proximal ends of the plurality of sutures 500 sequentially pass through the threading cavity 301 of the locking pin 300, the gap 25 between the first clip 221 and the second clip 223, the threading hole 2237, and then pass out of the threading groove 820 of the sleeve 82.

At step 3, the distal end of the forward-pushing release type suture locking device 100 is pushed into the right atrium of the heart through the femoral vein by aid of a guiding sheath (not shown) to move toward to the leaflets of the tricuspid valve while the sutures 500 are pulled until the distal end of the forward-pushing release type suture locking device 100 reaches a predetermined position in the right atrium.

At step 4, the tightness of the sutures 500 on the anterior leaflet, the posterior leaflet, and the septal leaflet is adjusted respectively, the least state of tricuspid valve regurgitation is determined through medical imaging equipment such as echocardiogram. When this state is reached, the adjustment is stopped, and the tightness of the two or three sets of sutures 500 is maintained, that is, a relative distance between the anterior leaflet, the posterior leaflet, and the septal leaflet of the tricuspid valve is maintained.

Figure 18:
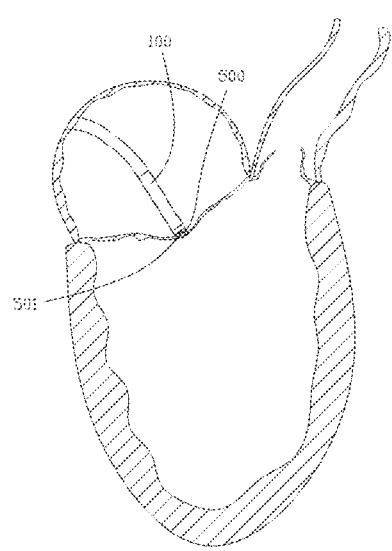
Figure 22:
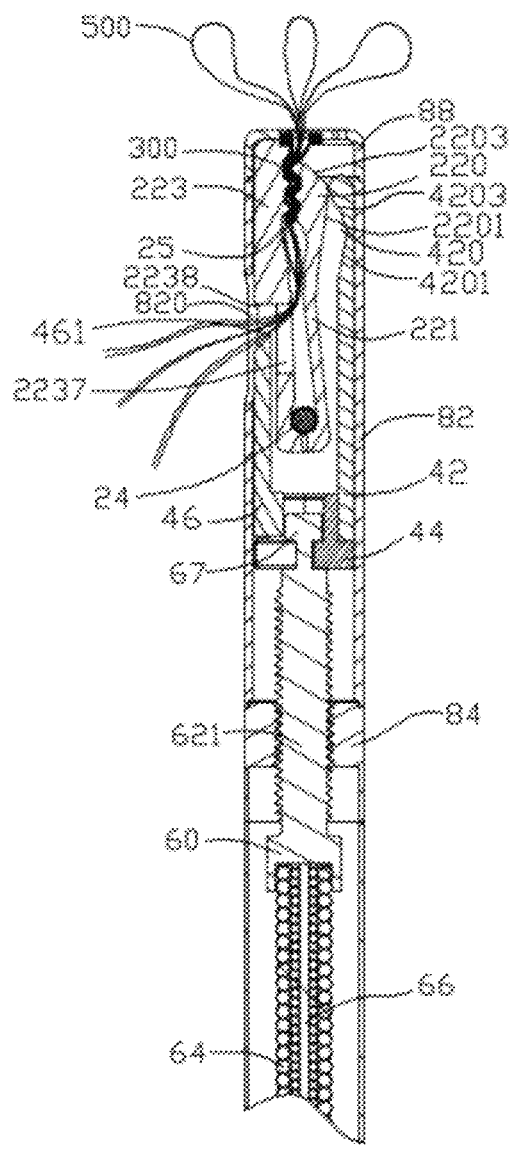

At step 5, as shown in FIG. 18 and FIG. 22, when the driving member 70 on the handle 90 rotates, the thread transmission member 62 moves to the distal end in the axial direction while rotating to drive the driving member 70, the flexible inner core 63, and the thread transmission member 62 to rotate and move distally in the axial direction, and the thread transmission member 62 pushes against the thrust rod assembly 40, to allow the thrust rod assembly 40 to move distally in the axial direction. During the process of moving the thrust rod assembly 40 distally in the axial direction, the thrust rod 42 is movable toward the distal end relative to the collet 22, and the distal end of the thrust rod 42 continuously pushes and squeezes the first outer slope 2201 on the first clip 221, until reaching the highest point of the protruding portion 220, so that the first clip 221 is driven to close to the second clip 223, and the locking pin 300 accommodated in the gap 25 is compressed by the first clip 221 and the second clip 223, until the locking pin 300 is deformed, and the two or three sets of sutures 500 are locked in the locking pin 300 together.

Figure 23:
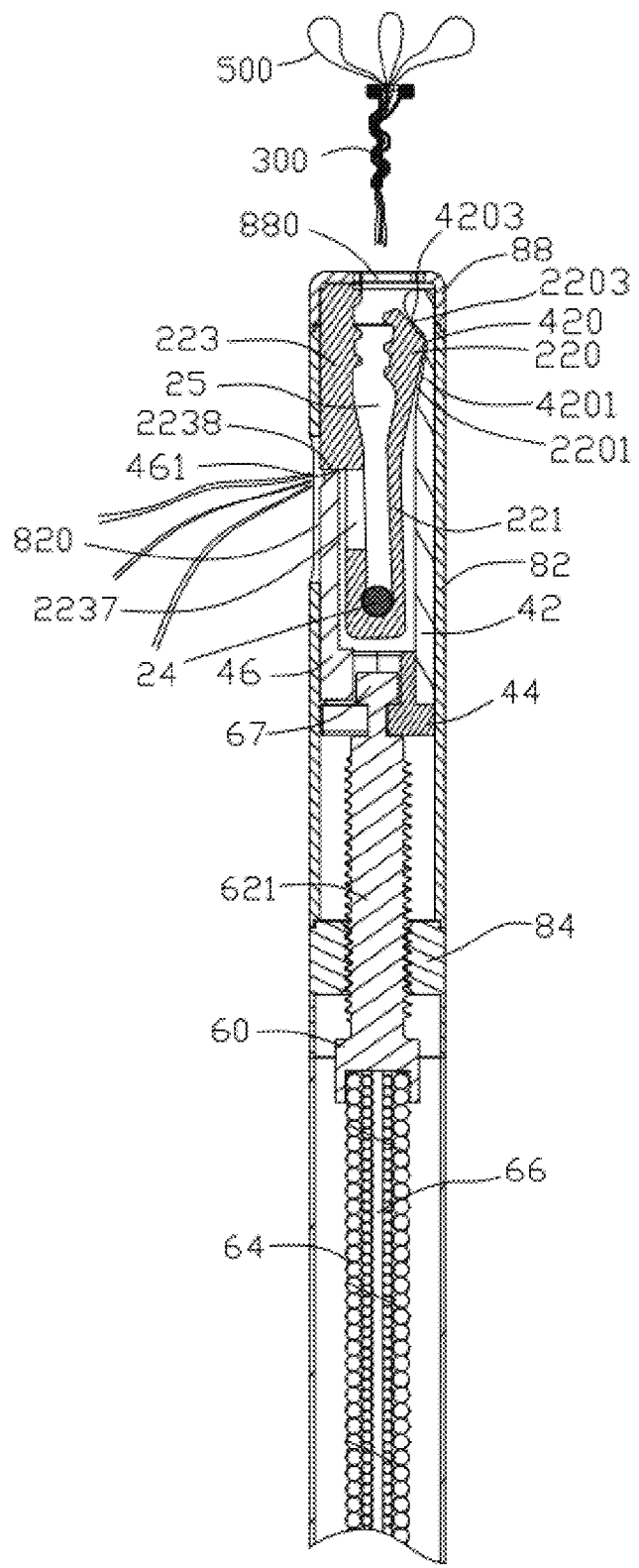

At step 6, as illustrated in FIG. 19, FIG. 20, and FIG. 23, when the driving member 70 on the handle 90 continues to rotate in the same direction, the thread transmission member 62 continues to move towards the distal end in the axial direction to drive the thrust rod 42 to continue to move distally in the axial direction, until the protruding portion 220 on the first clip 221 falls into the recessed portion 420 of the thrust rod 42, the collet 22 releases the locking pin 300, the cutting member 46 cuts the plurality of sutures 500, such that the locking pin 300 is released from the gap 25 of the collet 22, and then the plurality of sutures 500 are drawn outside the patient.

At step 7, the distal end of the forward-pushing release type suture locking device 100 is withdrawn from the patient, the locking pin 300 is remained in the patient, and the locking pin 300 fixes the two or three sets of sutures 500 that respectively implanted into the anterior leaflet, the posterior leaflet, and the septal leaflet together. The repair of the anterior leaflet, the posterior leaflet, and the septal leaflet of the tricuspid valve is completed.

It will be appreciated that in the above description, the forward-pushing release type suture locking device which is used for performing the interventional tricuspid valve repair process is taken as an example to illustrate a use procedure of the disclosure, and the forward-pushing release type suture locking device of the present disclosure can also be used for locking and fixing sutures in other surgical procedures.

Figure 25:
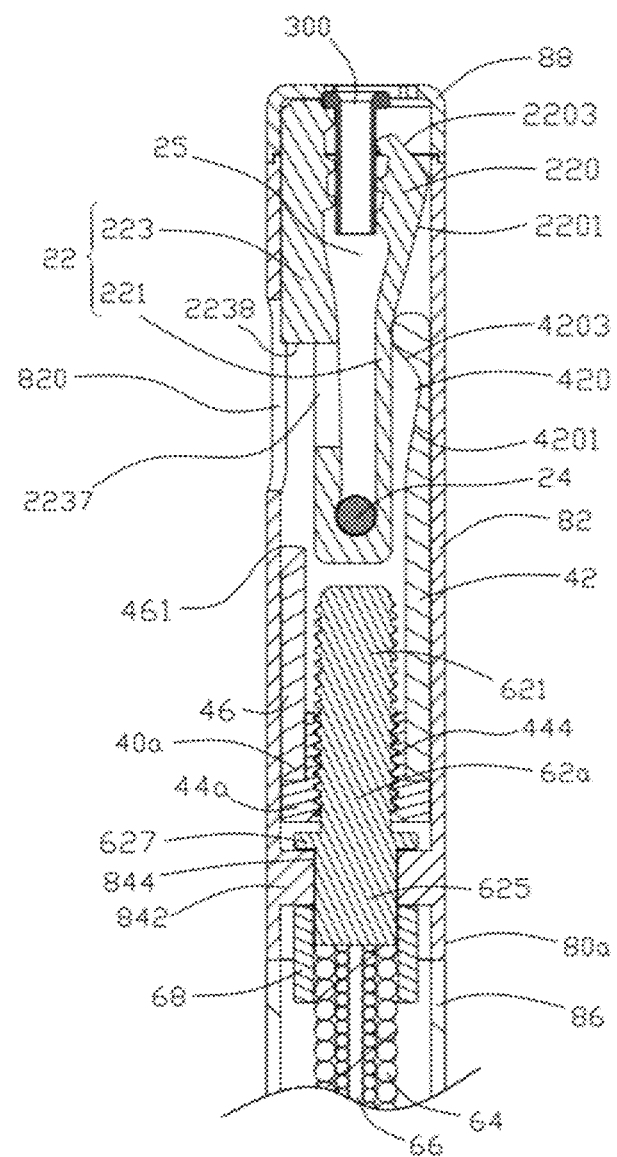
FIG. 25 is a schematic structural view of a forward-pushing release type suture locking device provided by a second implementation of the present disclosure.

As illustrated in FIG. 25, a structure of the forward-pushing release type suture locking device provided by the second embodiment of the present disclosure is similar to that of the first embodiment, the difference is: The structures of the thrust rod assembly 40a and the thread transmission member 62a provided in the second are slightly different from those of the first embodiment, and a connection structure of the thrust rod assembly 40a and the thread transmission member 62a is slightly different from that of the first embodiment. Details are as follows.

In the second embodiment, the forward-pushing release type suture locking device also includes a collet 22, a thrust rod assembly 40a, a transmission assembly, and an outer sleeve assembly 80a. The thread transmission member 62a is rotatably coupled to the outer sleeve assembly 80a, and the thread transmission member 62a and the thrust rod assembly 40a are threaded for transmission. The thread transmission member 62a only rotates, and the rotation of the thread transmission member 62a is converted into the movement of the thrust rod 42 in the axial direction through the threaded transmission between the thread transmission member 62a and the thrust rod assembly 40a.

The thread transmission member 62a includes a transmission screw rod 621 at the distal end and a connection rod 625 extending from a proximal end of the transmission screw rod 621 in the axial direction. A stepping 627 is provided on an outer wall of the proximal end of the transmission screw rod 621 in radial direction.

The pedestal 44a of the thrust rod assembly 40a in the second embodiment is provided with a screw hole 444 on the basis of the structure of the thrust rod assembly 40 in the first embodiment, and the transmission screw rod 621 is screwed with the screw hole 444.

The outer sleeve assembly 80a omits the connection sleeve of the outer sleeve assembly 80 in the first embodiment. An annular flange 842 is arranged on an inner wall of the sleeve 82 corresponding to the thread transmission member 62a. A proximal end of the thread transmission member 62a is rotatably inserted into the flange 842. An outer peripheral wall of the thread transmission member 62a is provided with the stepping 627 at a distal end of the flange 842. A fixing ring 68 is fixedly coupled to the thread transmission member 62a at a proximal end of the flange 842. A rotating groove is enclosed by the stepping 627 and the fixing ring 68, and the flange 842 is rotatably received in the rotating groove. The distal end of the flexible outer tube 86 is fixedly coupled to the proximal end of the sleeve 82. Since the stepping 627 is retained at the distal surface of the flange 842 and the fixing ring 68 is retained at the proximal surface of the flange 842, the connection rod 625 and the thread transmission member 62a can only rotate and cannot move in the axial direction.

In the embodiment, because the connection sleeve 84 is omitted, and the transmission screw rod 621 of the thread transmission member 62a is directly connected to the pedestal 44a of the thrust rod assembly 40a through the threaded transmission, so as to save more space.

The use of the forward-pushing release type suture locking device of the second embodiment is similar to that of the first embodiment, except that when the driving member on the handle rotates, the rotation of the driving member drives the flexible inner core and the thread transmission member 62a rotates in place, and the pedestal 44a drives the thrust rod 42 to move toward the distal end relative to the collet 22.

It will be appreciated that, without departing from the principles of the embodiments of the present disclosure, the specific technical solutions in the above embodiments are applicable to each other, and will not be repeated here.

The above is the implementation manners of this application. It should be pointed out that those of ordinary skill in the art may also make several improvements and modifications without departing from the principle of the implementations of this application. These improvements and modifications shall fall within the scope of protection of this application.

What is claimed is:

1. A forward-pushing release type suture locking device, which is configured to fix a suture in a locking pin, comprising:
   a collet; and
   a thrust rod assembly sleeved outside the collet;
   wherein a distal end of the collet is configured to accommodate the locking pin, and the collet is elastic;
   the thrust rod assembly comprises a thrust rod; a recessed portion is arranged at a side of the thrust rod faced toward the collet, a protruding portion corresponding to the recessed portion is arranged at a side of the collet faced toward the thrust rod;
   in a process that the thrust rod continuously moves distally in an axial direction, the thrust rod first pushes against a gradually raised side of the protruding portion, so as to allow the collet to deform to compress the locking pin, and allow the locking pin compressed by the collet to deform and fix the suture; and then the protruding portion is gradually accommodated in the recessed portion, so that at least part of deformations of the collet is restored to release the locking pin.

2. The forward-pushing release type suture locking device of claim 1, wherein the protruding portion comprises a first outer slope and a second outer slope intersecting with the first outer slope; the first outer slope gradually rises from a proximal end of the first outer slope to a distal end of the first outer slope, and the second outer slope gradually decreases from a proximal end of the second outer slope to a distal end of the second outer slope.

3. The forward-pushing release type suture locking device of claim 2, wherein an angle formed between the first outer slope and the second outer slope of the protruding portion is greater than or equal to 120 degrees, and less than 180 degrees.

4. The forward-pushing release type suture locking device of claim 3, wherein an inclination of the first outer slope is less than an inclination of the second outer slope; and when the collet is in a natural state, an angle formed between the first outer slope and a vertical plane perpendicular to the axial direction is greater than or equal to 70 degrees, and less than 90 degrees; and an angle formed between the second outer slope and the vertical plane perpendicular to the axial direction is greater than or equal to 50 degrees and less than 90 degrees.

5. The forward-pushing release type suture locking device of claim 2, wherein a height difference between the distal end and the proximal end of the first outer slope is greater than or equal to a diameter of a hole defined inside the locking pin, and is less than an outer diameter of the locking pin.

6. The forward-pushing release type suture locking device of claim 2, wherein a smooth transition is provided between the first outer slope and the second outer slope of the protruding portion; and a smooth transition is provided between a distal surface of the thrust rod and a surface of the thrust rod fitted to the collet.

7. The forward-pushing release type suture locking device of claim 2, wherein the recessed portion is arranged at a distal end of the thrust rod, the recessed portion includes a first inner slope and a second inner slope intersecting with the first inner slope; and when the protruding portion is accommodated in the recessed portion, the first outer slope corresponds to the first inner slope, and the second outer slope corresponds to the second inner slope.

8. The forward-pushing release type suture locking device of claim 7, wherein an angle formed between the first inner slope and the second inner slope of the recessed portion is greater than or equal to an angle formed between the first outer slope and the second outer slope of the protruding portion.

9. The forward-pushing release type suture locking device of claim 8, wherein when the collet is in a natural state, an angle formed between the first inner slope and a vertical plane perpendicular to the axial direction is greater than or equal to an angle formed between the first outer slope and the vertical plane perpendicular to the axial direction; and an angle formed between the second inner slope and the vertical plane perpendicular to the axial direction is greater than or equal to an angle formed between the second outer slope and the vertical plane perpendicular to the axial direction.

10. The forward-pushing release type suture locking device of claim 7, wherein a maximum depth of the recessed portion is greater than or equal to a maximum height of the protruding portion.

11. The forward-pushing release type suture locking device according to claim 7, wherein a smooth transition is provided between the second inner slope and a surface of the thrust rod fitted to the collet.

12. The forward-pushing release type suture locking device according to claim 1, wherein the forward-pushing release type suture locking device further comprises a transmission assembly coupled to the thrust rod assembly, the transmission assembly comprises a thread transmission member and a flexible inner core fixedly coupled to the thread transmission member, and the thread transmission member is rotatably coupled to the thrust rod assembly; the flexible inner core rotates to drive the thread transmission member to rotate, and the thread transmission member rotates to drive the thrust rod to move along the axial direction.

13. The forward-pushing release type suture locking device according to claim 12, wherein the forward-pushing release type suture locking device further comprises an outer sleeve assembly surrounding the collet, the thrust rod assembly, and the transmission assembly; the outer sleeve assembly comprises a sleeve and a flexible outer tube fixedly coupled to the sleeve, the collet and the thrust rod assembly are accommodated in the sleeve, and the collet is fixedly coupled to the sleeve, and the flexible outer tube is sleeved outside the flexible inner core.

14. The forward-pushing release type suture locking device according to claim 13, wherein the thread transmission member is a transmission screw rod; a distal end of the thread transmission member is rotatably coupled to the thrust rod assembly through a connection portion, and the thread transmission member moves in the axial direction while rotates to drive the thrust rod to move in the axial direction.

15. The forward-pushing release type suture locking device according to claim 13, wherein the thread transmission member is a transmission screw rod; the thread transmission member is directly screwed with the thrust rod assembly, and the thread transmission member only rotates to drive the thrust rod to move along the axial direction.

16. The forward-pushing release type suture locking device according to claim 12, wherein the forward-pushing release type suture locking device further comprises a driving member, the driving member is fixedly coupled to a proximal end of the flexible inner core, and the driving member is configured to drive the flexible inner core and the thread transmission member to rotate.

17. The forward-pushing release type suture locking device according to claim 16, wherein the forward-pushing release type suture locking device further comprises a handle, and the driving member is rotatably arranged at a proximal end of the handle.

18. The forward-pushing release type suture locking device according to claim 12, wherein the thrust rod assembly further comprises a cutting member arranged on an opposite side of the thrust rod.

19. The forward-pushing release type suture locking device according to claim 18, wherein a distal end of the cutting member is provided with a blade configured to cut the suture.

20. The forward-pushing release type suture locking device according to claim 1, wherein the protruding portion is arranged at a distal end of the collet, and the recessed portion is arranged at a distal end of the thrust rod.

* * * * *